United States Patent
Yamada

(10) Patent No.: US 9,126,003 B2
(45) Date of Patent: Sep. 8, 2015

(54) CUFF-EQUIPPED TUBE

(75) Inventor: Masayuki Yamada, Tokyo (JP)

(73) Assignees: Masayuki Yamada, Tokyo (JP); Daiken Medical Co., Ltd., Osaka (JP)

( * ) Notice: Subject to any disclaimer, the term of this patent is extended or adjusted under 35 U.S.C. 154(b) by 163 days.

(21) Appl. No.: 13/392,291

(22) PCT Filed: May 12, 2010

(86) PCT No.: PCT/JP2010/058045
§ 371 (c)(1),
(2), (4) Date: Feb. 24, 2012

(87) PCT Pub. No.: WO2011/024519
PCT Pub. Date: Mar. 3, 2011

(65) Prior Publication Data
US 2012/0145159 A1    Jun. 14, 2012

(30) Foreign Application Priority Data

Aug. 25, 2009  (JP) .................................. 2009-194022
Apr. 8, 2010   (JP) .................................. 2010-089605

(51) Int. Cl.
*A61M 16/00*   (2006.01)
*A61M 16/04*   (2006.01)
*A61M 25/10*   (2013.01)

(52) U.S. Cl.
CPC ........... *A61M 16/04* (2013.01); *A61M 16/0445* (2014.02); *A61M 16/0434* (2013.01); *A61M 25/10* (2013.01); *A61M 25/1002* (2013.01); *A61M 25/1034* (2013.01)

(58) Field of Classification Search
CPC .......................... A61M 16/04–16/0497; A61M 25/10–25/1011
USPC ........ 128/207.14–207.17, 200.26; 604/96.01, 604/97.01; 606/192
See application file for complete search history.

(56) References Cited

U.S. PATENT DOCUMENTS

| | | | | |
|---|---|---|---|---|
| 2,892,458 | A  * | 6/1959 | Auzin | 604/103.06 |
| 4,147,169 | A  * | 4/1979 | Taylor | 604/102.02 |
| 6,221,042 | B1 * | 4/2001 | Adams | 604/96.01 |
| 6,517,492 | B2   | 2/2003 | Koblanski | |
| 6,550,475 | B1   | 4/2003 | Oldfield | |
| 6,745,773 | B1   | 6/2004 | Gobel | |
| 6,942,640 | B2 * | 9/2005 | Kokish | 604/96.01 |
| 7,207,972 | B2   | 4/2007 | Flodin | |
| 7,849,857 | B2   | 12/2010 | Gobel | |

(Continued)

FOREIGN PATENT DOCUMENTS

| | | |
|---|---|---|
| CN | 2208423 Y | 9/1995 |
| CN | 1498092 A | 5/2004 |

(Continued)

*Primary Examiner* — Steven Douglas
*Assistant Examiner* — Kathrynn Reilly
(74) *Attorney, Agent, or Firm* — The Webb Law Firm

(57) ABSTRACT

A cuff-equipped tube formed by providing a cuff to the outer periphery of a flexible tube, the cuff being expanded by introducing an operation fluid thereinto or being contracted by discharging the operation fluid therefrom. The cuff is provided with a cuff affixing portion expanded outward by the introduction of the operation fluid thereinto, and also with one mounting portion and the other mounting portion that are mounted to the outer peripheral surface of the tube. The connecting portions of the cuff affixing portion and the one mounting portion is affixed in a constricted shape to the outer peripheral surface of the tube, and the connecting portions of the cuff affixing portion and the other mounting portion is affixed in a constricted shape to the outer peripheral surface of the tube.

2 Claims, 10 Drawing Sheets

(56) References Cited

U.S. PATENT DOCUMENTS

| | | |
|---|---|---|
| 7,987,851 B2 | 8/2011 | Blom et al. |
| 8,225,795 B2 * | 7/2012 | Pell .................... 128/207.15 |
| 2004/0138625 A1 | 7/2004 | Flodin |
| 2007/0144526 A1 * | 6/2007 | Blom et al. ............. 128/207.16 |
| 2007/0295337 A1 * | 12/2007 | Nelson et al. ............ 128/207.15 |
| 2008/0053454 A1 * | 3/2008 | Pasillas et al. ........... 128/207.15 |
| 2009/0014009 A1 | 1/2009 | Chen et al. |
| 2011/0011406 A1 | 1/2011 | Blom et al. |

FOREIGN PATENT DOCUMENTS

| | | |
|---|---|---|
| CN | 1791441 A | 6/2006 |
| DE | 19638935 C1 | 3/1998 |
| GB | 2328615 A | 3/1999 |
| JP | 2002505925 A | 2/2002 |
| JP | 2004508905 A | 3/2004 |
| JP | 2006528524 A | 12/2006 |
| JP | 2007175500 A | 7/2007 |
| WO | 02051490 A1 | 7/2002 |

* cited by examiner

CUFF-EQUIPPED TUBE

TECHNICAL FIELD

The present invention relates to a cuff-equipped tube. More specifically, the present invention relates to a cuff-equipped tube in which a cuff is disposed on the outer periphery of a tube that can be change in shape like a differential lung ventilation apparatus.

BACKGROUND ART

In a chest surgery for instance, as disclosed in Patent Literature 1, it is necessary that a thin flexible tube is inserted into a trachea to a bronchial tube of a patient, an apical end part is disposed at an appropriate position, the lungs are divided and blocked, and a flexible cuff-equipped tube that can be change in shape is inserted in order to supply an air to other lung.

As described above, for a cuff-equipped tube that is used for carrying out a surgical procedure to a patient, after a cuff that has been attached to a flexible tube that can be change in shape is inserted up to an appropriate position, the operation fluid such as air is introduced to the cuff to expand the cuff, and an outer surface of the cuff is pressurized to the inner wall of a trachea, whereby the cuff and the tube are affixed to a position and an air leakage efficiency is ensured.

However, even in the case in which the cuff and the tube are affixed to a position as described above, in the case in which a body posture of a patient is changed later to ensure an operative field, the cuff that has been affixed once is moved from the predetermined position by an external force. As a result, the air leakage efficiency cannot be ensured in some cases in the case of a differential lung ventilation apparatus for instance, and there is a possibility that a predetermined gas such as an air cannot be supplied from a gas delivery port of an apical end opening of the tube to a desired lung. In this case, it is necessary that the tube is inserted again and a position of the cuff is adjusted.

In particular, in the case in which a cuff is expanded and affixed in a shorter bronchial tube that is located below a bifurcation of the trachea like a differential lung ventilation apparatus, when a position gap of a cuff occurs and a cuff is dislocated to a bifurcation of the trachea, an air leakage efficiency cannot be maintained and an adjustment of a position is required again. However, an operation for adjusting a position of a flexible tube again causes a medical treatment to be suspended and a burden to be increased on a patient unfavorably.

A blood vessel, a bile duct, an esophagus, a trachea, a urethra, a living organism lumen of other organ, or a narrow area in a body cavity is expanded by a cuff as a medical procedure for not only a differential lung ventilation apparatus. Even in such a case, an affixing position of a cuff is dislocated and a desired medical treatment cannot be carried out in some cases.

In the case in which a position gap occurs for a cuff-equipped tube that is configured to carry out a medical procedure to other region in addition to a trachea, it is necessary that a cuff is contracted once to carry out a position adjustment again and the cuff is expanded again. Consequently, a time and an effort are required and an appropriate medical treatment is interrupted. Moreover, a burden is increased on a patient as a matter of course.

PRIOR ART DOCUMENTS

Patent Literature

[Patent Literature 1]
Japanese Unexamined Patent Application Publication No. 2002-505925

SUMMARY OF THE INVENTION

The present invention was made in consideration of such conditions, and an object of the present invention is to provide a cuff-equipped tube that can prevent a movement of a cuff as soon as practicably possible even in the case in which an external force for moving the cuff or the tube is applied in the case in which a body posture of a patient is changed by way of experiment after the cuff-equipped tube is inserted into the affected part of the body and the cuff is expanded to position the cuff and the tube.

In order to achieve the above object, a cuff-equipped tube in accordance with the present invention is characterized by comprising a cuff to the outer periphery of a flexible tube, the cuff being expanded by introducing an operation fluid thereinto or being contracted by discharging the operation fluid therefrom, wherein the cuff is provided with a cuff affixing portion that is expanded outward by the introduction of the operation fluid thereinto, and also with one mounting portion and the other mounting portion that are mounted to the outer peripheral surface of the tube, a connecting portion of the one mounting portion and the cuff affixing portion is affixed in a constricted shape to the outer peripheral surface of the tube, and a connecting portion of the other mounting portion and the cuff affixing portion is affixed in a constricted shape to the outer peripheral surface of the tube, and in the case in which an external force is applied to the cuff affixing portion in a state in which the operation fluid is introduced to the cuff affixing portion and the cuff affixing portion is expanded, the distance between the one mounting portion and the other mounting portion is constant and does not change and the cuff affixing portion is located at a predetermined position, and in the case in which the external force that has been applied to the tube is removed, the cuff affixing portion returns to the original posture.

A cuff-equipped tube in accordance with the present invention is characterized in that the cuff is formed in a generally barrel shape in which the cuff affixing portion is expanded to the both sides from an axis core as a center, the one mounting portion and the other mounting portion are extended outward in an axis direction of the cuff affixing portion in a barrel shape, and in the case in which the cuff is affixed to the outer peripheral surface of the tube, the one mounting portion is pushed into the side of the other mounting portion in such a manner that the one mounting portion is partially overlapped with the cuff affixing portion, the other mounting portion is pushed into the side of the one mounting portion in such a manner that the other mounting portion is partially overlapped with the cuff affixing portion, and each of the mounting portions is affixed to the outer peripheral surface of the flexible tube in this posture.

A cuff-equipped tube in accordance with the present invention is characterized in that the cuff is formed in a generally barrel shape in which the cuff affixing portion is expanded to the both sides from an axis core as a center, the one mounting portion and the other mounting portion are extended outward in an axis direction of the cuff affixing portion in a barrel shape, a connecting portion of the one mounting portion and the cuff affixing portion is formed in advance in a constricted shape, a connecting portion of the other mounting portion and the cuff affixing portion is formed in advance in a constricted shape, and in the case in which the cuff is affixed to the outer peripheral surface of the tube, each of the connecting portions is affixed in a constricted shape to the outer peripheral surface of the flexible tube.

A cuff-equipped tube in accordance with the present invention is characterized in that the cuff is formed in a generally barrel shape in which the cuff affixing portion is expanded to the both sides from an axis core as a center, the one mounting portion and the other mounting portion are extended outward in an axis direction of the cuff affixing portion in a barrel shape, and in the case in which the cuff is affixed to the outer peripheral surface of the tube, each of the one mounting portion and the cuff affixing portion is turned inside out, and the one mounting portion and the cuff affixing portion that have been turned inside out are affixed to the outer peripheral surface of the flexible tube.

For a cuff-equipped tube that has been formed as described above, even in the case in which an external force for moving a cuff that has been affixed in advance is applied, a deformation of the cuff enables the external force to be absorbed.

A cuff-equipped tube in accordance with the present invention is characterized in that the cuff affixing portion, the one mounting portion, and the other mounting portion are formed in a generally cylindrical shape, and in the case in which the cuff is affixed to the outer peripheral surface of the tube, a connecting portion of the cuff affixing portion and the one mounting portion is pushed inside in a constricted shape, a connecting portion of the cuff affixing portion and the other mounting portion is pushed inside in a constricted shape, and the connecting portions are affixed to the outer peripheral surface of the flexible tube.

For a cuff-equipped tube that is configured as described above, even in the case in which an external force for moving a cuff that has been affixed once in a bronchial tube is applied, a deformation force of the cuff enables the external force to be absorbed.

Advantageous Effects of Invention

For the cuff-equipped tube in accordance with the present invention, even in the case in which an external force is applied to a cuff in the state in which the cuff has been positioned once to an abutted part such as an inner wall of a trachea when a body posture of a patient is changed for instance, a tube is moved by the external force and a main part of a cuff affixing portion is not moved from original position in which the cuff has been positioned to an abutted part. Moreover, since an air leakage efficiency of a cuff is ensured, an appropriate medical treatment is not interrupted.

Moreover, in the case in which the external force applied to the tube is removed, the cuff returns to the original attitude and a position of the cuff affixing portion is not changed. In accordance with the present invention as described above, an operation to insert the tube again is not necessary. By this configuration, it is not necessary to carry out an operation in which a burden is increased on the patient.

DETAILED DESCRIPTION OF THE INVENTION

A cuff-equipped tube in accordance with the present invention will be described below in detail with reference to the drawings.

Figure 1:
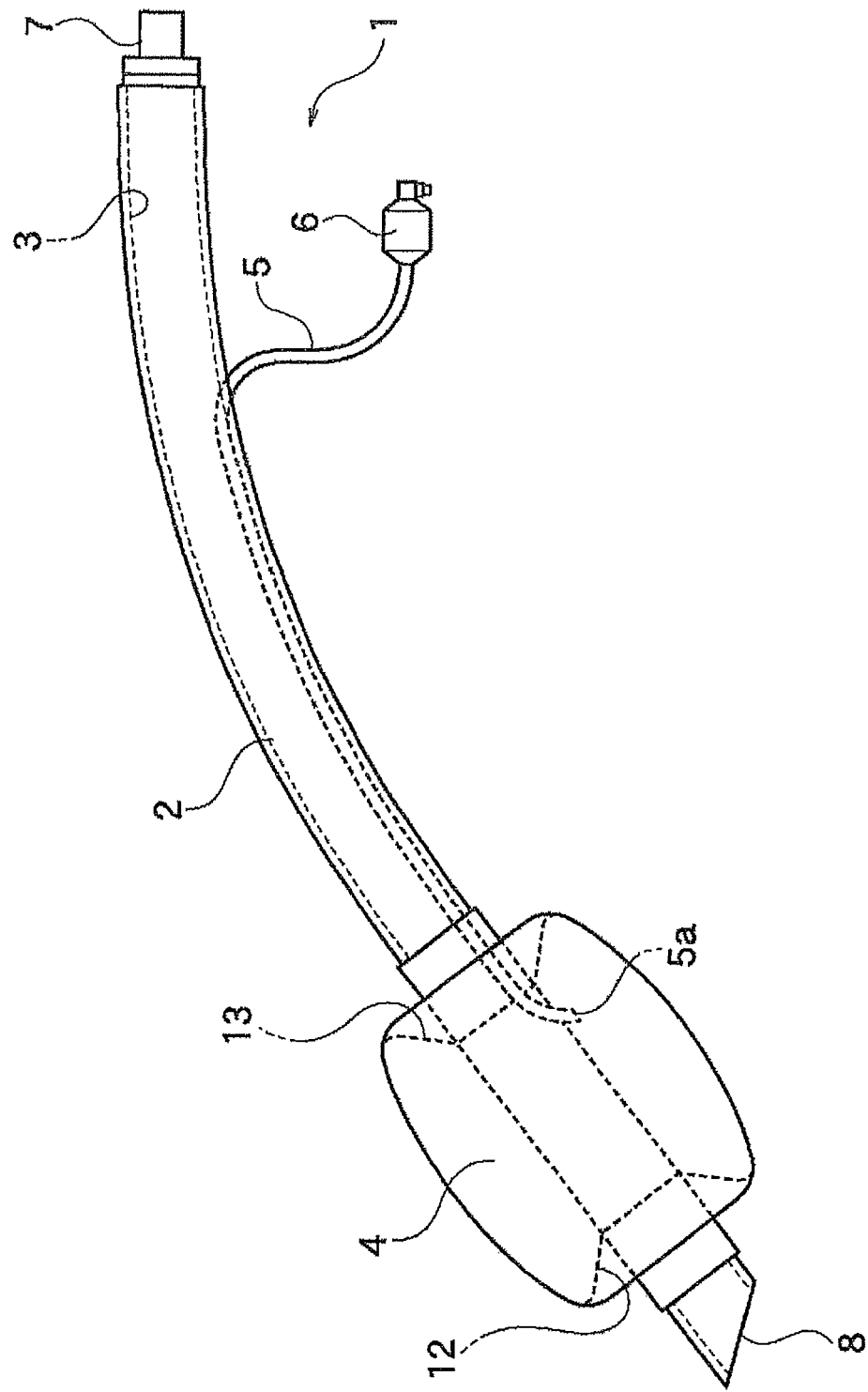
FIG. 1 is a schematic diagrammatic perspective view showing a cuff-equipped tube in accordance with an embodiment of the present invention.

FIG. 1 is a schematic diagrammatic perspective view showing a cuff-equipped tube in accordance with an embodiment of the present invention.

For a cuff-equipped tube 1, a cuff 4 capable of performing an expansion and a contraction is disposed around an apical end opening 8 of a through hole 3 that has been formed in a flexible tube 2. A narrow tube 5 that is configured to introduce an operation fluid such as an air into the cuff 4 is disposed along the inner wall of the tube 2. The apical end opening 5a of the narrow tube 5 is disposed in the cuff 4. The cuff 4 shown in FIG. 1 is indicated in a state in which an operation fluid has been introduced.

As a material of the above flexible tube 2, there can be mentioned for instance polymer materials having flexible property including a polyamide resin or a polyamide elastomer such as nylon 11, nylon 12, and nylon 610, a polyolefin such as polypropylene and polyethylene, an olefin based elastomer such as a polyethylene elastomer and a polypropylene elastomer, a polyester such as polyethylene terephthalate, soft polyvinyl chloride, a polyurethane and a polyurethane elastomer, a fluorine resin and a fluorine resin based elastomer such as polytetrafluoroethylene, a polyimide, an ethylene vinyl acetate copolymer, and a silicone rubber, although not restricted in particular thereto. One kind or at least two kinds of the above materials can be combined to be used.

By forming the flexible tube 2 with the above materials, the flexible tube 2 is provided with an appropriate flexible property and a self-independent retention property.

On the other hand, the cuff 4 is configured by a film member in a tubular shape with a wide variety of high polymer materials (in particular, a thermoplastic resin). While the cuff 4 is provided with a flexible property as a whole, it is preferable that the cuff 4 is configured by a material with a comparatively low extensibility (a small coefficient of extension). By this configuration, in the case in which the cuff 4 is expanded, the cuff 4 can be prevented from being pushed back by receiving a reaction force from an inner wall of a trachea or the like.

As a material of the cuff 4, there can be mentioned for instance materials including a polyamide resin or a polyamide elastomer such as nylon 11, nylon 12, and nylon 610, a polyester such as polyethylene terephthalate (PET), a natural rubber, a polyolefin copolymer, and an ethylene vinyl acetate copolymer, soft polyvinyl chloride, a polyurethane, a polyisoprene, a polyimide, a polyimide elastomer, polytetrafluoroethylene, silicone, and a polymer blend or a polymer blend that includes at least one kind of the above materials.

The cuff 4 is provided with a pilot balloon 6 that is provided with a valve system. In the case in which a predetermined operation fluid such as air is introduced from the pilot balloon 6 to the cuff 4 via a narrow tube 5, the cuff 4 is expanded outward as shown in FIG. 1. Moreover, in the case in which an operation fluid is discharged from the pilot balloon 6 via the narrow tube 5, the cuff 4 is returned to be in a contracted state.

An adapter 7 is connected to a head part of the tube 2, and a predetermined fluid such as air is supplied into the tube 2 by the connection of the adapter 7 with an apparatus not shown.

For the cuff-equipped tube 1 that has been formed as described above, after the operation fluid such as an air in the cuff is degassed and the cuff-equipped tube 1 is slightly curved at its posture, the tube 2 is inserted into a trachea for instance. After it is confirmed that the cuff 4 reaches the predetermined position, the cuff 4 is expanded by introducing an appropriate operation fluid via the pilot balloon 6 and a narrow tube 5 into the cuff 4. By this configuration, the external surface is abutted to the inner wall 15 of the trachea 14 as an abutted part shown in FIG. 3 for instance. Moreover, the cuff 4 of the cuff-equipped tube 1 is affixed in a certain manner, and the trachea 14 of a patient is blocked. After that, a predetermined gas such as an air is supplied from the adapter 7 into the tube 2, and the gas is sent from the apical end opening 8 of the tube 2 to be supplied into a bronchial tube.

Since the pilot balloon 6 shown in FIG. 1 is a balloon that is configured to predict a degree of an expansion of the cuff 4, the pilot balloon 6 is not always necessary.

The cuff 4 that is adopted in the present embodiment shown in FIG. 1 will be described below in more detail with reference to FIG. 2.

Figure 2:
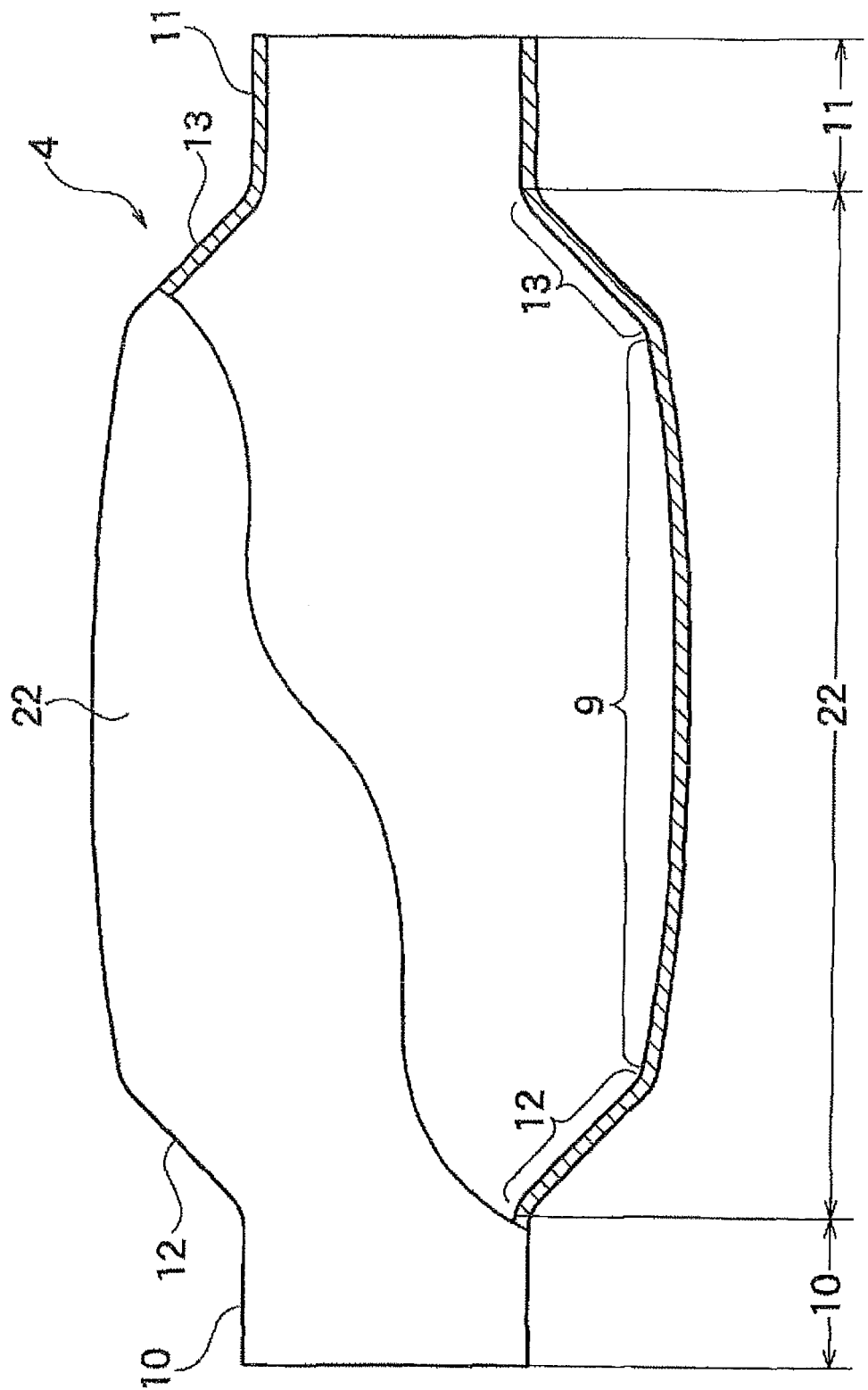
FIG. 2 is a front elevation view in the case in which a posture of a natural state of a cuff that is adopted as the cuff-equipped tube shown in FIG. 1 is partially broken for a cross-sectional view.

FIG. 2 is a front elevation view showing a posture in a generally natural state of the cuff 4 that has been fabricated by a blow molding or the like.

In the case in which the operation fluid is introduced in a state in which the both sides of the cuff 4 in accordance with the present embodiment are blocked, the cuff 4 is provided with a cuff affixing portion 22 in a tubular shape that is expanded outward at a generally central part, one mounting portion 10 on one end part of the cuff affixing portion 22, and the other mounting portion 11 on the other end part of the cuff affixing portion 22. The cuff affixing portion 22 is formed in a generally barrel shape.

The cuff affixing portion 22 is provided with tapered side walls 12 and 13 at the both end parts.

In the present invention, a main part 9 of the cuff affixing portion 22 is abutted to the inner wall 15 of the trachea 14 in the case in which the cuff 4 is expanded. However, a part of the tapered side walls 12 and 13 is abutted to the inner wall 15 and another part of the tapered side walls 12 and 13 is not abutted to the inner wall 15 depending on a degree of the expansion and a degree of a curvature of the inner wall 15.

Figure 3:
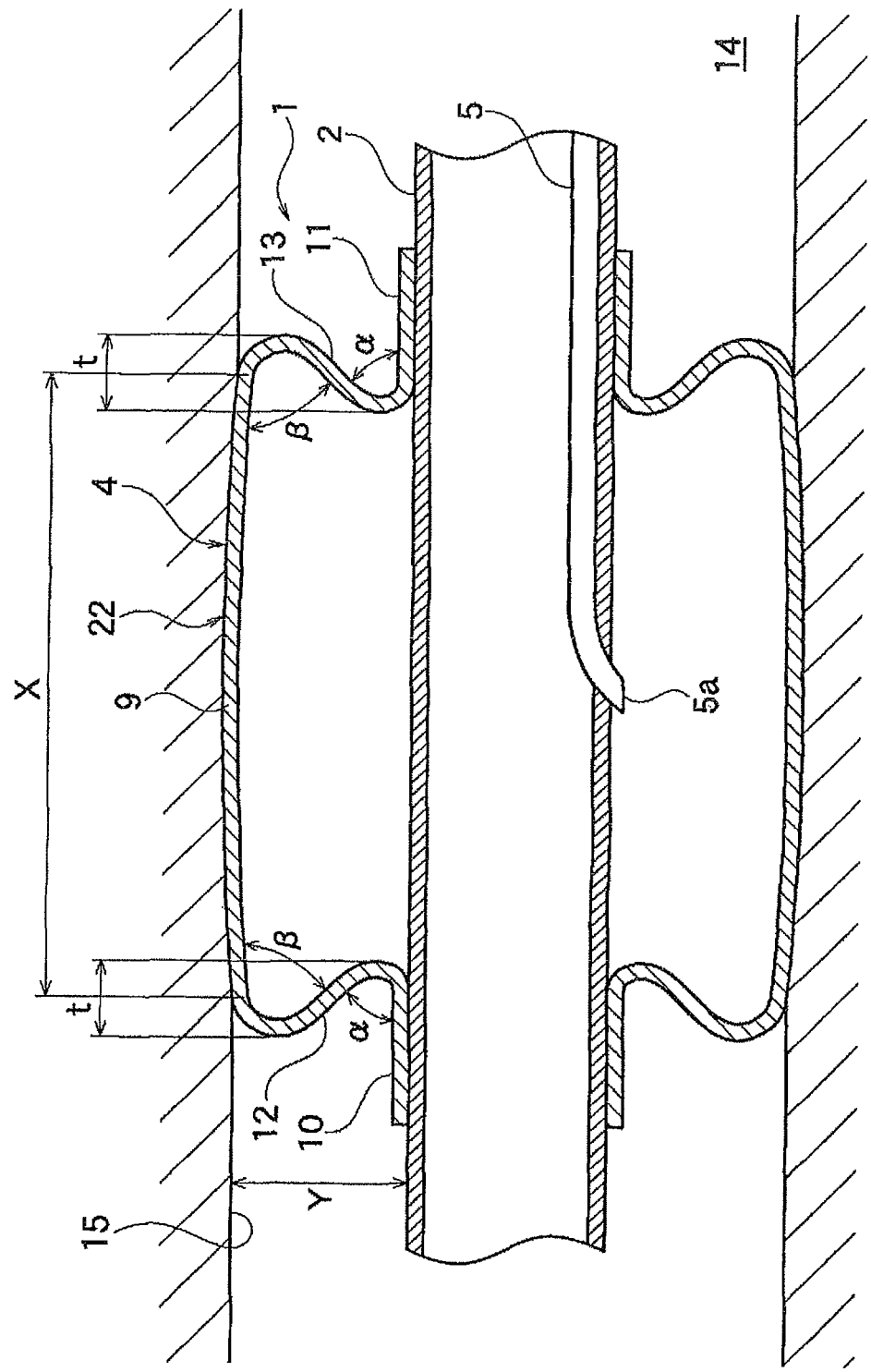
FIG. 3 is a schematic cross-sectional view in the case in which the operation fluid is introduced to a cuff of the cuff-equipped tube that is shown in FIG. 1 and that has been inserted into a trachea to expand the cuff and the cuff is abutted to an inner wall of the trachea.

As shown in FIG. 2, the cuff 4 that has been formed in such a manner that one mounting portion 10 and the other mounting portion 11 are projected outward in the axis direction of the cuff affixing portion 22 is affixed to the outer peripheral surface of the tube 2 in a posture that is shown not in FIG. 2 but in FIG. 1 and FIG. 3.

More specifically in the first place, one mounting portion 10 and the other mounting portion 11 are pushed toward the center side from each other from the posture shown in FIG. 2. By this procedure, one mounting portion 10, the tapered side wall 12, and the cuff affixing portion 22 are disposed in such a manner that the one mounting portion 10, the tapered side wall 12, and the cuff affixing portion 22 are partially overlapped to each other, and a generally Z shape is formed at this position in a state in which the cuff is abutted to the inner wall 15 as shown in FIG. 3. Similarly to this configuration, the other mounting portion 11, the tapered side wall 13, and the cuff affixing portion 22 are disposed in such a manner that the other mounting portion 11, the tapered side wall 13, and the cuff affixing portion 22 are partially overlapped to each other, and a generally Z shape is formed at this position in a state in which the cuff is abutted to the inner wall 15.

After the one mounting portion 10 and the other mounting portion 11 are pushed in such a manner that the mounting portion, the tapered side wall, and the cuff affixing portion are partially overlapped to each other, the cuff 4 is affixed to the outer peripheral surface of the tube 2 in such a manner that a distance between the one mounting portion 10 and the other mounting portion 11. The fixation of the one mounting portion 10 and the other mounting portion 11 to the tube 2 is carried out by using an adhesive agent or by a thermal fusion bonding. However, the method is not restricted in particular.

For the cuff-equipped tube 1 shown in FIG. 3, the angles of gradient $\alpha$ and $\beta$ are acute angles in a state in which the cuff 4 is affixed to the tube 2 as shown in the figure. In other words, since the both end parts are pushed toward the center side, a region in which the one mounting portion 10 and the cuff affixing portion 22 are overlapped with each other is formed, and the length of the overlapping is t. Moreover, a region in which the other mounting portion 11 and the cuff affixing portion 22 are overlapped with each other is formed, and the length of the overlapping is t.

It is necessary that an average length t of the overlapped region of one side mounting portion on the outer peripheral surface of the tube is at least 3 mm. In the case in which a movable length of the cuff 4 is in the range of 5 mm to 15 mm, it is preferable that the average length t of one side mounting portion is in the range of 5 mm to 10 mm.

Figure 4:
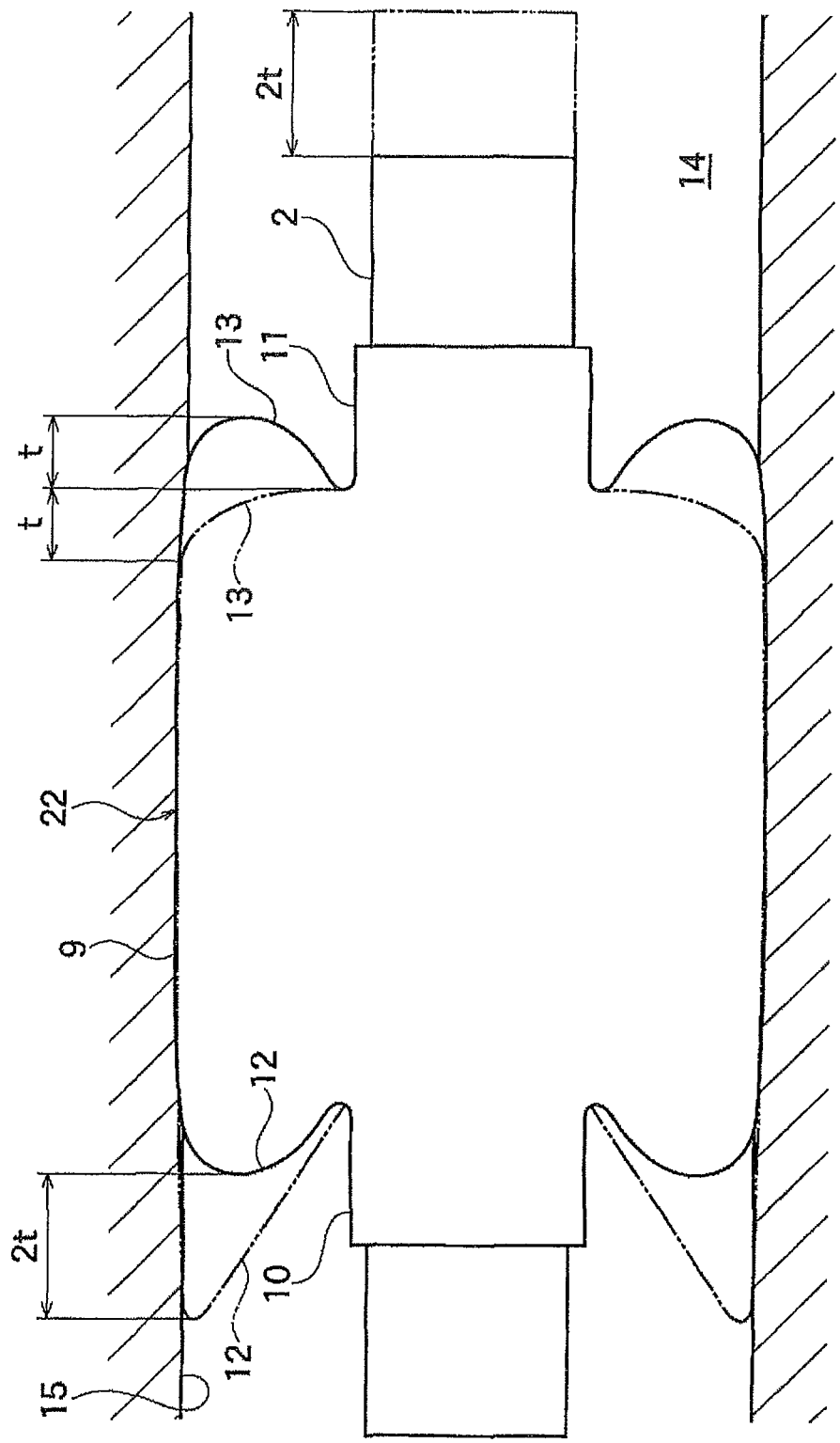
FIG. 4 is a schematic view showing a deformation enable region the cuff-equipped tube shown in FIG. 3 for instance.

In the case in which the average length t of the overlapped region is set to be in the above range in advance for a differential lung ventilation apparatus, when the tube 2 is moved to the right hand side of FIG. 4 by a distance of approximately 2 t in comparison to the trachea 14 as shown in FIG. 4, the tapered side walls 12 and 13 shown by a solid line is moved to a position shown by the alternate long and two short dashes line. However, the central main part 9 of the cuff affixing portion 22 is still fixed to the first position. Consequently, in the case in which the external force that has been applied to the tube 2 is removed, the tapered side walls 12 and 13 shown by the alternate long and two short dashes line in FIG. 4 return to the original position shown by a solid line. Moreover, since the main part 9 of the cuff affixing portion 22 is not moved in this return, an affixing position of a cuff 4 is not moved to the abutted part of the inner wall 15.

A usage example of the cuff-equipped tube 1 will be described in the following.

Figure 5:
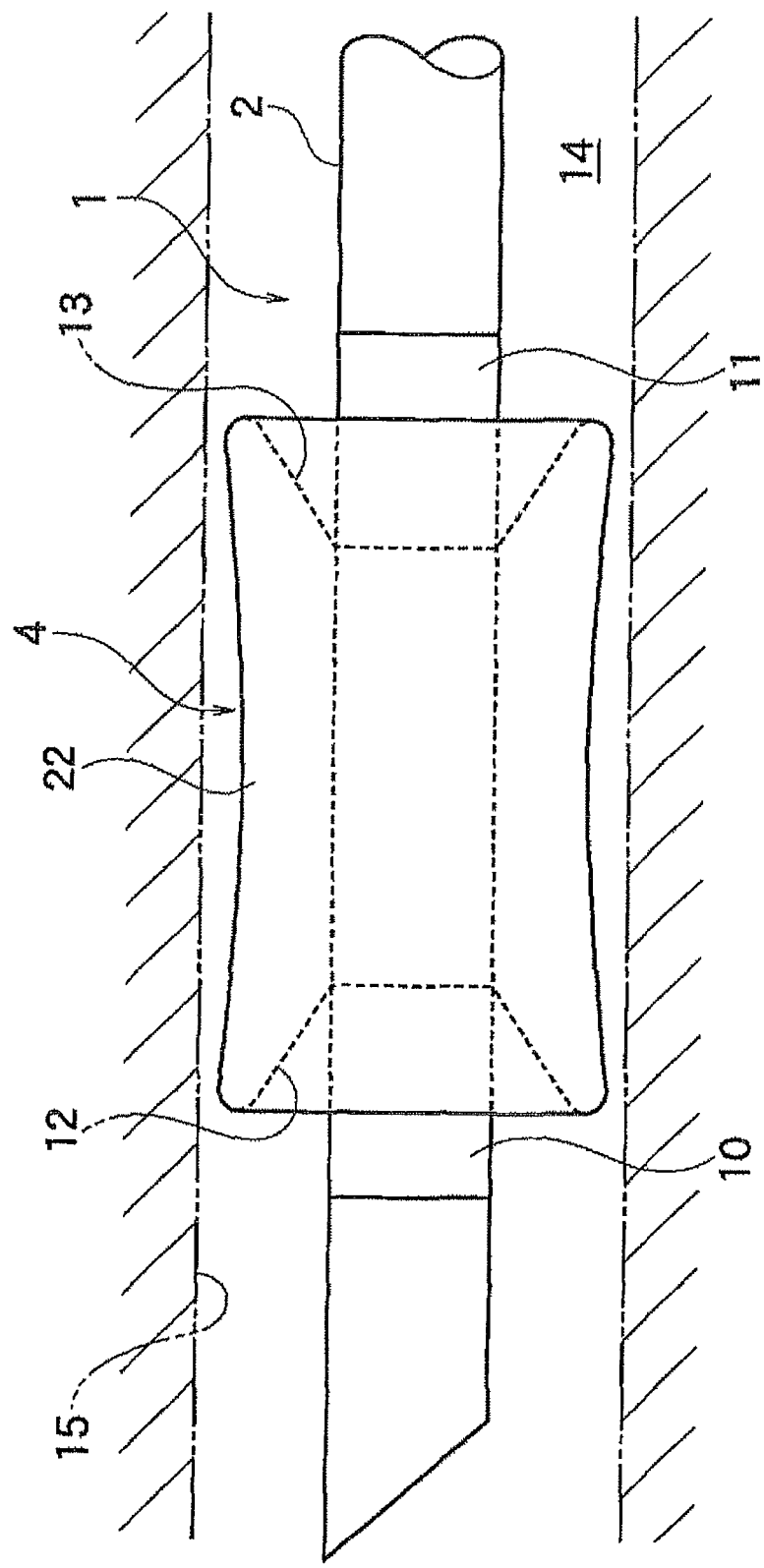
FIG. 5 is a schematic view in the case in which the cuff is inserted into a trachea without introducing the operation fluid to a cuff of the cuff-equipped tube that is shown in FIG. 1.

In the case in which the cuff 4 is inserted into a trachea 14 as shown in FIG. 5, the cuff 4 is set to be in a contracted state before being inserted. After it is confirmed that the cuff 4 is in a contracted state, the cuff-equipped tube 1 is inserted into a trachea 14. After it is then confirmed that the cuff 4 of an apical end part reaches the predetermined position, the operation fluid is introduced to the cuff 14 from an external part via the pilot balloon 6 and the narrow tube 5 shown in FIG. 1 to expand the cuff 4 outward. In the case in which the cuff 4 is expanded as described above, the main part 9 of the cuff affixing portion 22 of the cuff 4 is abutted to the inner wall 15 of the trachea 14 as shown in FIG. 3.

By this procedure, the cuff-equipped tube 1 is positioned and affixed in the trachea 14. In this state, the cuff 4 is fixed to the position unless a body posture of a patient is changed or an external force is applied to the tube 2. Moreover, the air leakage efficiency or the liquid leakage efficiency can be ensured in an outer peripheral section of the cuff. Furthermore, a predetermined gas such as air can be supplied to a bronchial tube of a downstream via the adapter 7 shown in FIG. 1 or the like. In this state moreover, a body fluid does not flow from a bronchial tube side (a left hand of FIG. 3) to a mouth side (a right hand of FIG. 3) on the boundary of the cuff affixing portion 22 that has been expanded, or from a mouth side to a bronchial tube side on the boundary of the cuff affixing portion 22.

In the next place, the following describes the case in which a body posture of a patient is changed or an external force is applied to the tube 2 from the state in which the cuff 4 is disposed at a predetermined position as shown in FIG. 3.

In the present specification, the case in which a body posture of a patient is changed or an external force is applied to the tube 2 is assumed in some range. An applied large force that exceeds a friction force of the cuff affixing portion 22 and the abutted part (the inner wall 15 of the trachea 14 in the case of the present embodiment) and a force that causes a movement of a tube that exceeds a range of motion of the cuff are not assumed.

In the case in which a body posture of a patient is changed for instance, a shape of the trachea 14 and a shape of a bronchial tube are three-dimensionally deformed, whereby a relative external force is applied to the tube 2. Consequently, a flexible tube 2 is moved to a mouth side of a patient (a right hand of FIG. 3, in a direction of an arrow A of FIG. 6). At this time, in a range that does not exceed a friction force of the cuff affixing portion and the abutted part, or in the case in which a movement distance of the tube 2 is smaller than a range of motion of the cuff 4, only the tube 2 is moved, and an affixing position of the cuff 4 is not moved.

Figure 6:
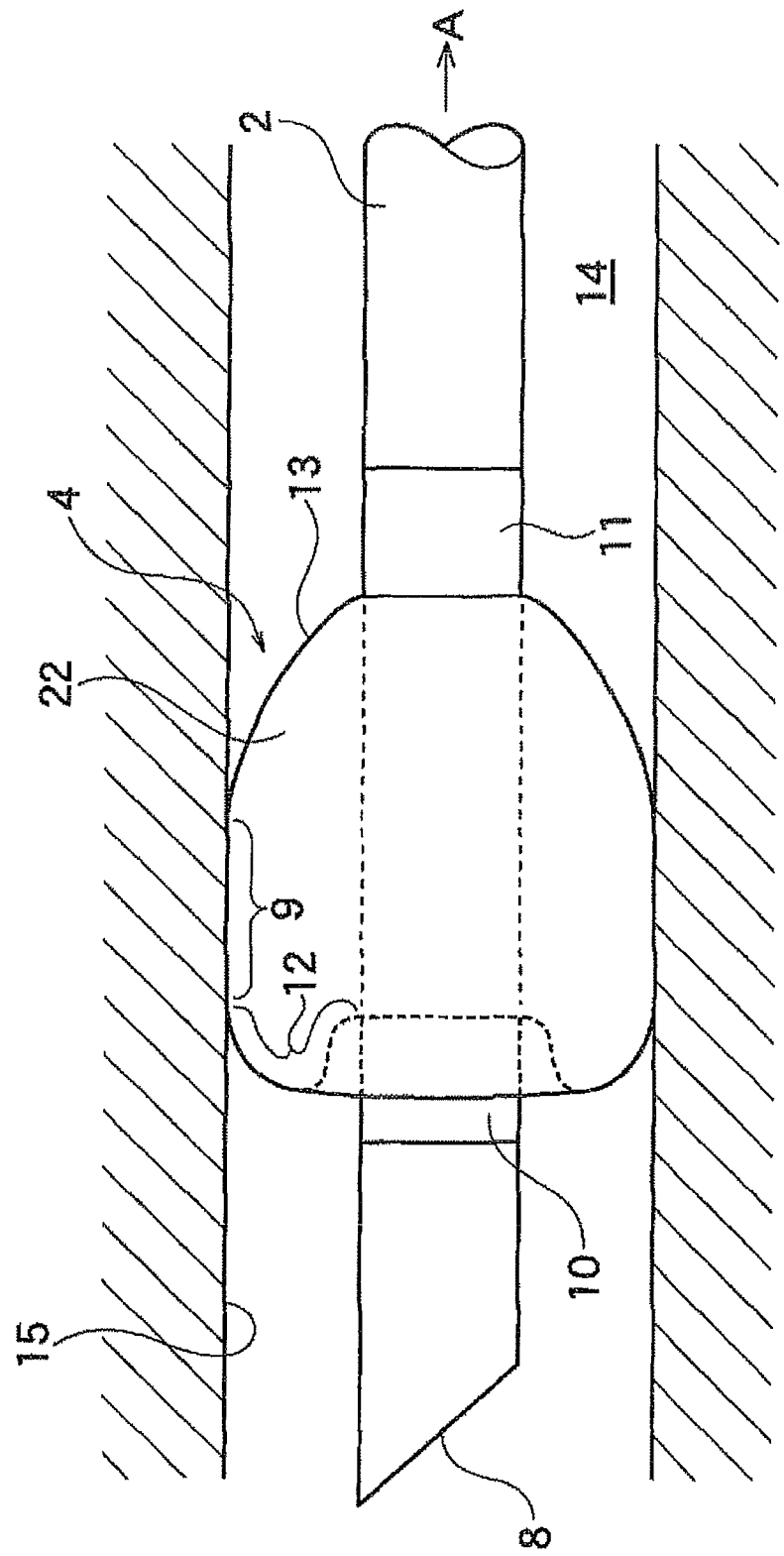
FIG. 6 is a schematic enlarged cross-sectional view in the case in which the operation fluid is introduced to a cuff of the cuff-equipped tube that is shown in FIG. 5, the cuff is affixed to an inner wall of the trachea, and the tube is moved in a direction of A.

That is, as shown in FIG. 3 or FIG. 6, the main part 9 of the cuff affixing portion 22 of the cuff 4 is abutted to the inner wall 15 of the trachea 14 and an affixing position of the cuff 4 is ensured. Consequently, even in the case in which a force is applied for moving the tube 2 in a direction of an arrow A in a relative manner due to a change of a body posture of a patient, a change of the posture occurs only for the tapered side walls 12 and 13, and the posture of the main part 9 is not changed. The tapered side wall 12 is inflected greatly for instance and the other tapered side wall 13 is in an extended posture as shown in FIG. 6.

At this time, since the main part 9 of the cuff affixing portion 22 that has been expanded is still being abutted to the inner wall 15 at a predetermined pressure, the cuff 4 is not moved against the abutted part, that is, the inner wall 15 of the trachea 14. Moreover, the cuff 4 is still being affixed in a state in which the main part 9 of the cuff affixing portion 22 is expanded, the air leakage efficiency can be ensured.

In the case in which the external force that has been applied to the tube 2 is removed from the posture shown in FIG. 6, the tube 2 is moved in the opposite direction of a direction of an arrow A, and the tapered side wall 12 and the other tapered side wall 13 return to the original posture shown in FIG. 3.

In the present embodiment, a posture of any one of the tapered side wall 12 and the other tapered side wall 13 is inflected in such a manner that the tapered side wall 12 or the other tapered side wall 13 gains entry inside greatly as shown in FIG. 6, the part in a constricted shape can be used as a liquid puddle. Consequently, even in the case in which a body fluid tries to flow to the opposite side over the cuff 4, the body fluid can be trapped by the constricted part.

In accordance with the present embodiment as described above, in the case in which an external force for moving the cuff 4 is applied in the case in which a body posture of a patient is changed by way of experiment after the cuff 4 is inserted into the affected part of the body and the cuff 4 is fixed, an affixing position of the cuff 4 to the patient is dislocated, whereby it is not necessary that a positioning is carried out again. By this configuration, it is not necessary to carry out an operation in which a burden is increased on the patient.

While the preferred embodiments in accordance with the present invention have been described above, the present invention is not restricted to the embodiments.

For instance, the above embodiment describes the case in which a body posture of a patient is changed and the tube 2 is moved in a direction of an arrow A shown in FIG. 6. However, even in the case in which the tube 2 is moved in the opposite direction of a direction of an arrow A, an affixing position of a cuff 4 is not changed. Moreover, even in the case in which an external force is applied in such a manner that the tube 2 is rotated not in a straight line direction but in a circumferential direction, when the external force that has been applied to the tube 2 is removed, the cuff 4 can be returned to the original posture.

Moreover, a setting of a range of motion of the tube 2 for still affixing the cuff 4 to the first position can be carried out by adjusting a length t shown in FIG. 3 and FIG. 4 in an appropriate manner. In order to improve a friction force to an abutted part, a friction force can be increased by lengthen a length Y of a radial direction to a length X of an axial direction of the cuff affixing portion 22 shown in FIG. 3, and the movability of the cuff can also be adjusted.

The embodiment shown in FIG. 1 to FIG. 6 describes the example in which one mounting portion 10 and the other mounting portion 11 that have been formed on the both sides of the cuff affixing portion 22 are pushed toward the center side to be affixed. However, the present invention is not restricted to this example.

Figure 7:
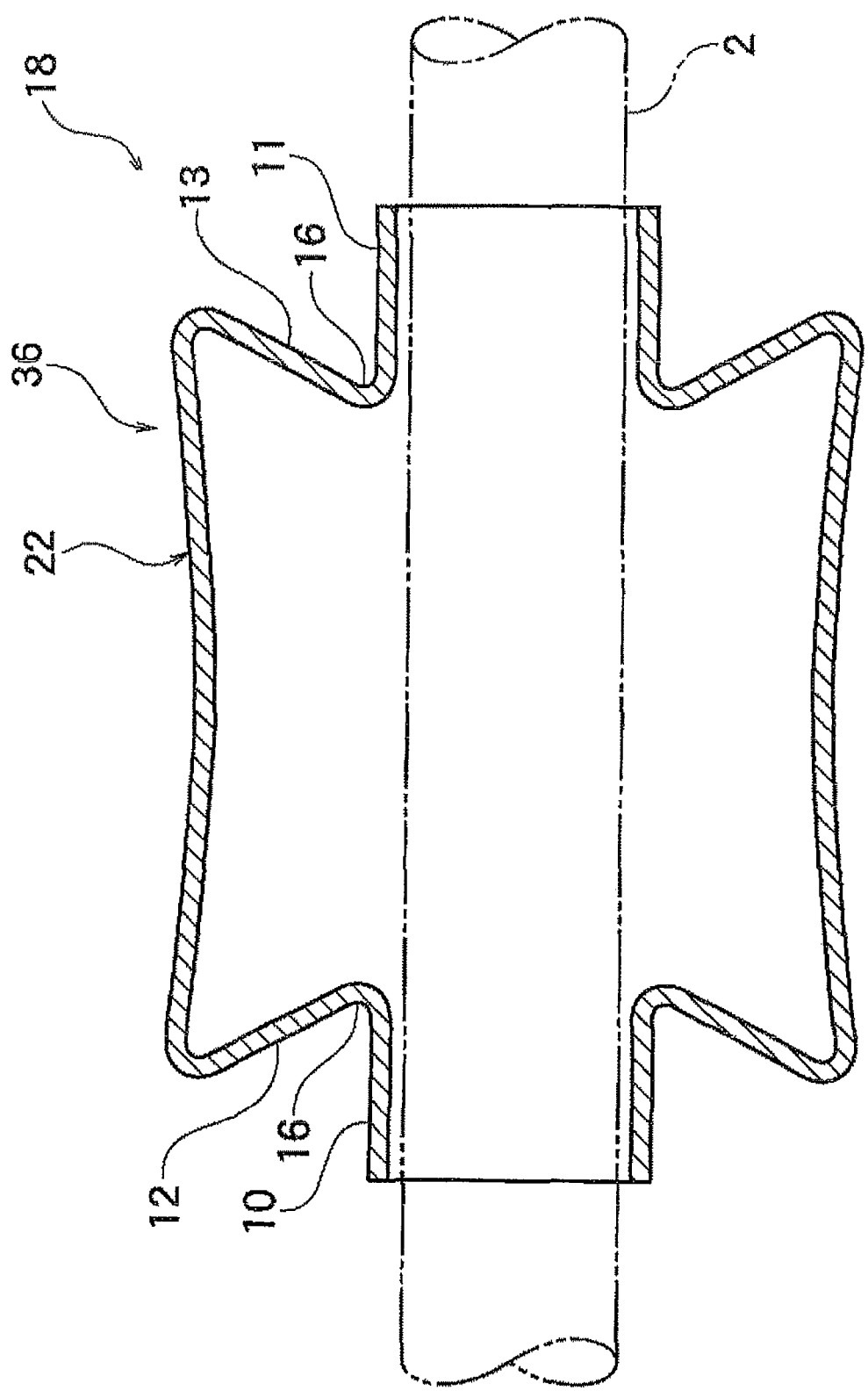
FIG. 7 is a schematic main part cross-sectional view showing a cuff of a cuff-equipped tube in accordance with another embodiment of the present invention.

For instance, like a cuff-equipped tube 18 of another embodiment that is shown in FIG. 7, a connecting portion 16 of the one mounting portion 10 and the tapered side wall 12 can be formed in a constricted shape, and similarly a connecting portion 16 of the other mounting portion 11 and the tapered side wall 13 can be formed in a constricted shape in manufacturing the cuff 36.

In other words in the present embodiment, a generally Z shape is formed in advance by the one mounting portion 10, the tapered side wall 12, and the cuff affixing portion 22 of the cuff 36, and similarly a generally Z shape is formed in advance by the other mounting portion 11, the tapered side wall 13, and the cuff affixing portion 22 of the cuff 36.

For the cuff-equipped tube 18 of another embodiment that is shown in FIG. 7, the cuff 36 is attached to the periphery of the tube 2 in a posture in manufacturing as shown in FIG. 7.

Even in the case in which the connecting portion 16 is formed in a constricted shape like the cuff 36 that has been adopted in the cuff-equipped tube 18, in the case in which the operation fluid is introduced to the cuff 36 to expand the cuff affixing portion 22 and the cuff affixing portion 22 is abutted to the abutted part, a function effect that is similar to that of the case of the cuff-equipped tube 1 shown in FIG. 3 can be obtained. Moreover, even in the case in which an external force is applied to the tube 2, a distance between the one mounting portion 10 and the other mounting portion 11 is not changed.

Figure 8:
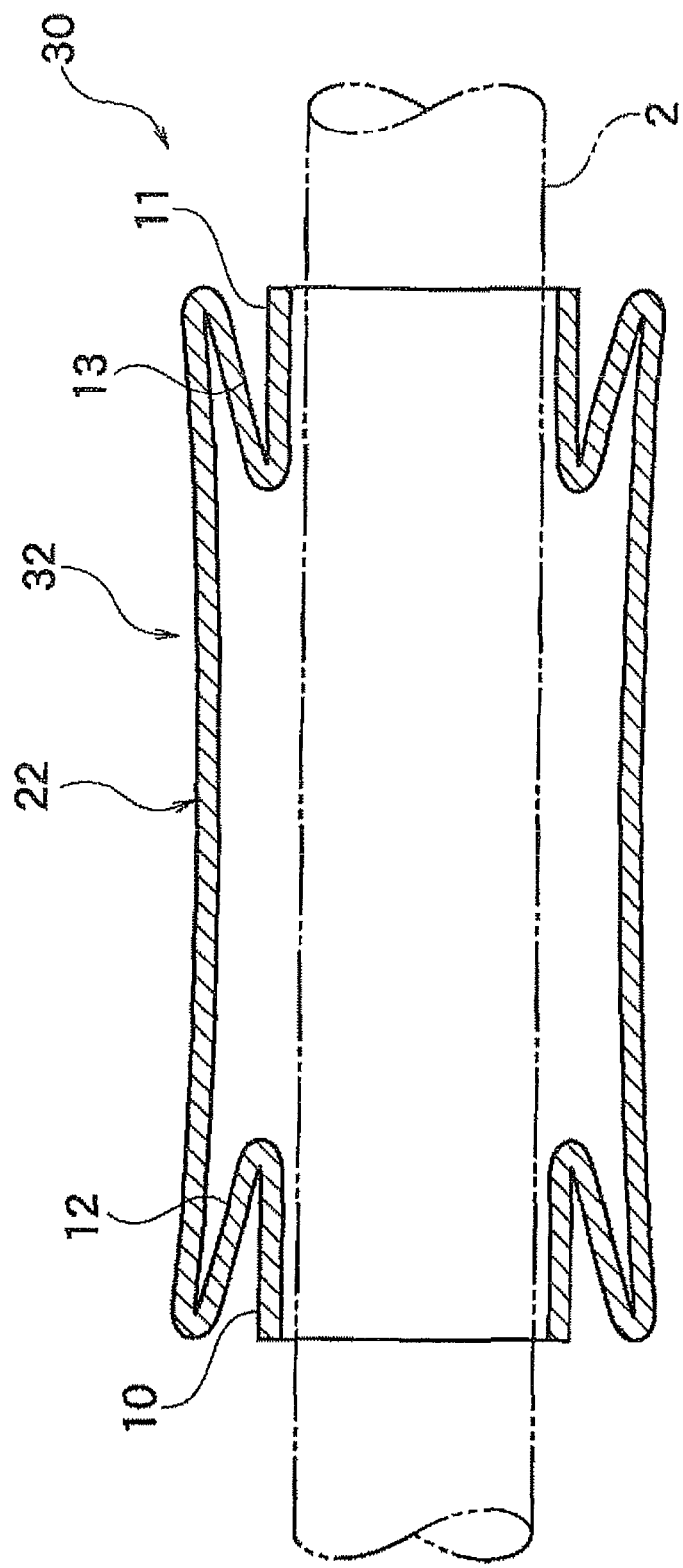
FIG. 8 is a schematic main part cross-sectional view showing a cuff of a cuff-equipped tube in accordance with more another embodiment of the present invention.
Figure 9:
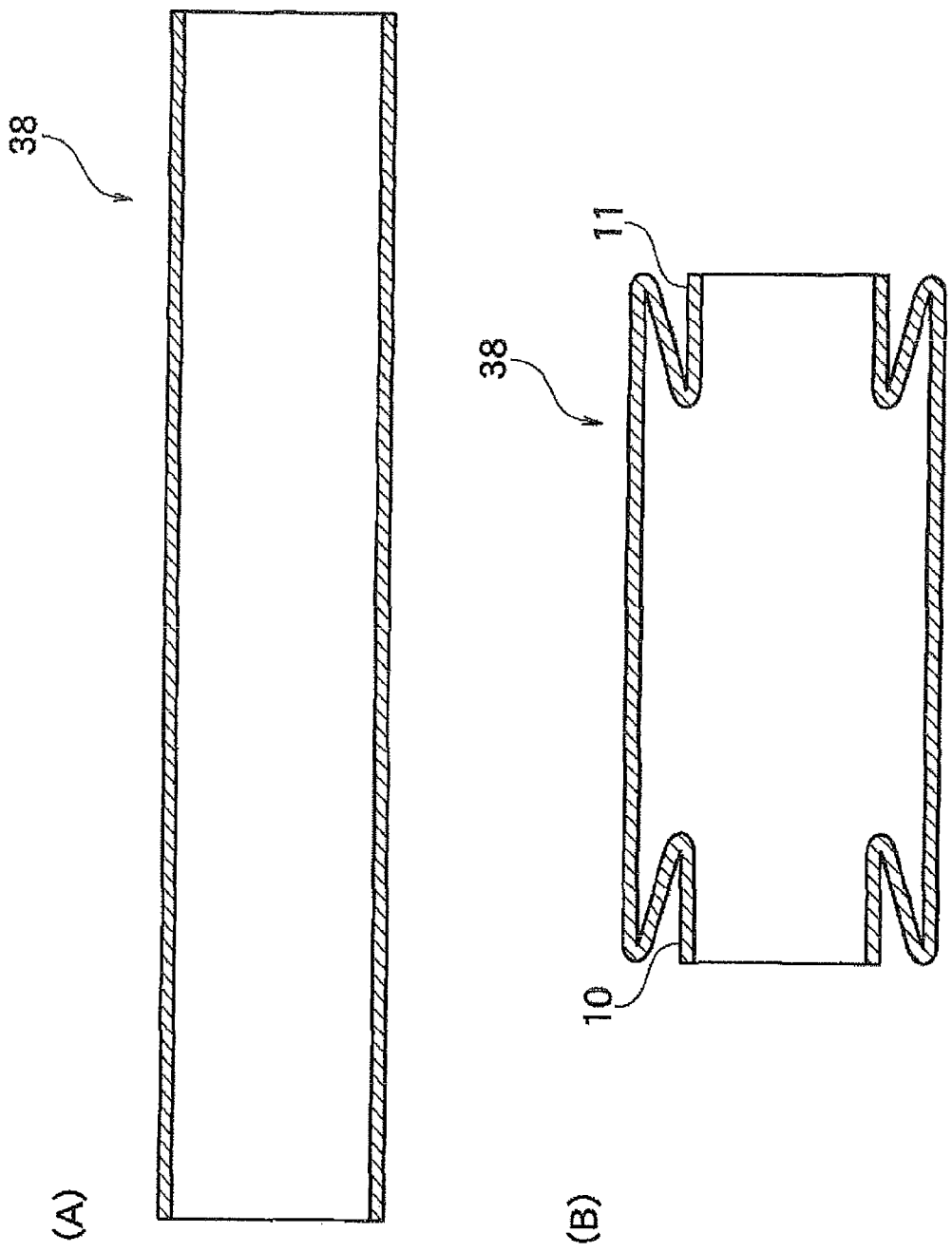
FIG. 9(A) is a schematic cross-sectional view showing a cuff material that is adopted for a cuff-equipped tube that is shown in FIG. 8 in accordance with more another embodiment of the present invention.
FIG. 9(B) is a schematic cross-sectional view showing a cuff that has been formed in such a manner in which the cuff material that is shown in FIG. 9(A) is folded back.

FIG. 8 is a schematic view showing a cuff-equipped tube 30 in accordance with more another embodiment of the present invention. FIG. 9(A) and FIG. 9(B) are schematic views showing a cuff material 38 before forming the cuff 32 shown in FIG. 8.

As shown in FIG. 9(A), the cuff material 38 is formed in a generally cylindrical shape. By pushing the both end parts of the cuff material 38 in a generally cylindrical shape toward the center side as shown in FIG. 9(B), the one mounting portion 10 and the other mounting portion 11 are formed to be affixed to the tube 2. In this state, the cuff-equipped tube 30 of FIG. 8 can be formed by affixing the cuff material 38 to the outer peripheral surface of the tube 2 without changing a distance between the one mounting portion 10 and the other mounting portion 11.

Even in the case of the cuff-equipped tube 30 in which the cuff 32 is made of the cuff material 38 in a generally cylindrical shape, a function effect that is similar to that of the case of the cuff-equipped tube 1 of the embodiment shown in FIG. 3 can be obtained by introducing the operation fluid into the cuff 32. That is, even in the case in which an external force is applied to the cuff 32, a distance between the one mounting portion 10 and the other mounting portion 11 is not changed.

For the "generally cylindrical shape" in the present embodiment, even in the case in which the center part of the cuff material 38 is slightly expanded outward and the cuff material 38 is formed in a "barrel shape", the cuff material 38 is also in a "generally cylindrical shape".

Figure 10:
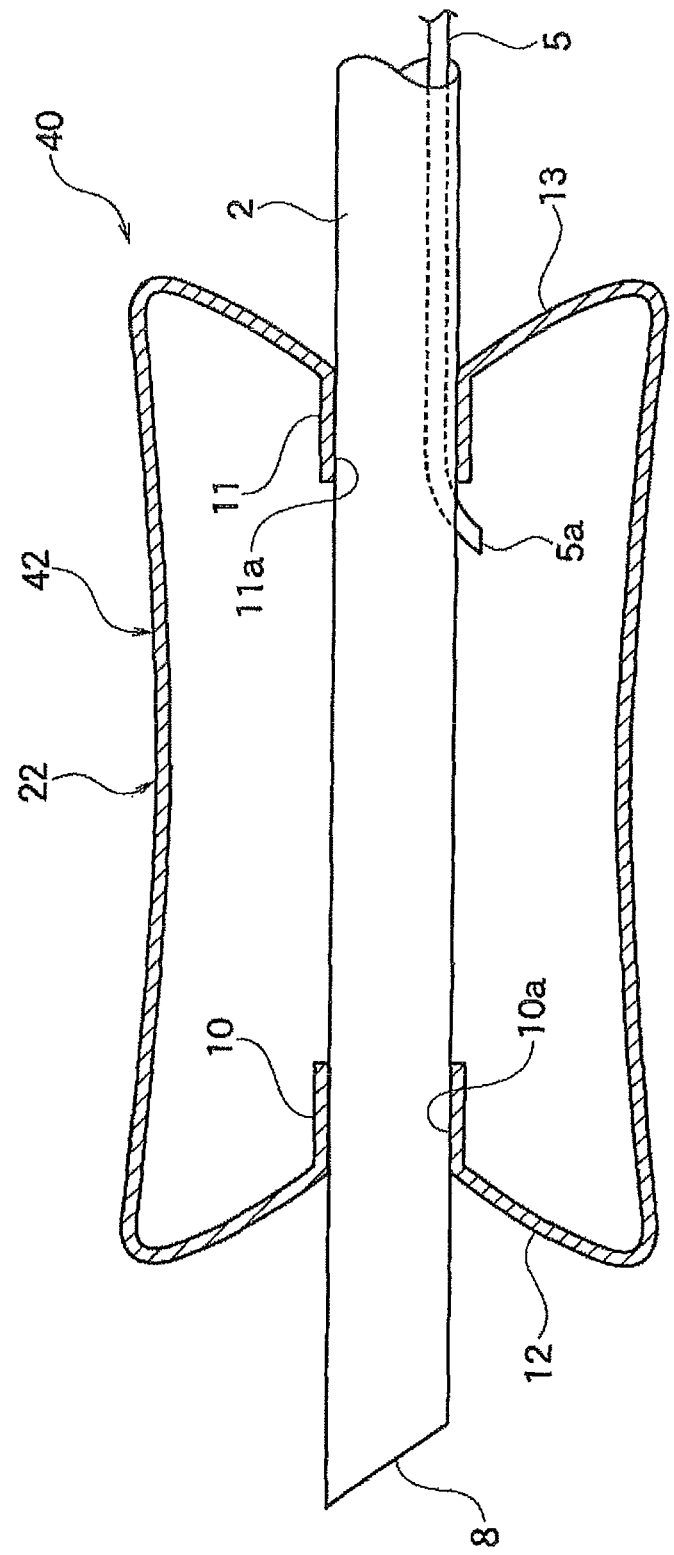
FIG. 10 is a schematic cross-sectional view showing a cuff-equipped tube in accordance with more another embodiment of the present invention in which a cuff is used in such a manner in which the cuff that is shown in FIG. 7 is folded back.

FIG. 10 is a schematic view showing a cuff-equipped tube 40 in accordance with more another embodiment of the present invention. The cuff 42 in accordance with the present embodiment is formed in a shape that is similar to the shape of the cuff 36 shown in FIG. 7. However, as a different point, the one mounting portion 10 and the other mounting portion 11 are mounted to the tube 2 in a posture in which the one mounting portion 10 and the other mounting portion 11 are folded back.

Even in the case of the cuff-equipped tube 40 in which the one mounting portion 10 and the other mounting portion 11 are mounted to the tube 2 in a posture in which the one mounting portion 10 and the other mounting portion 11 are folded back like the cuff 42 shown in FIG. 10, a function effect that is similar to that of the case of the cuff-equipped tube 1 of the embodiment shown in FIG. 3 can be obtained by introducing the operation fluid into the cuff 42 to be expanded.

In the above embodiments, the cuff-equipped tube in which one tube 2 is provided with one cuff 4 is described. However, as substitute for this configuration, the present invention can also be applied to a cuff-equipped tube in which one tube is provided with at least two cuffs. In addition, the present invention can also be applied to a cuff-equipped tube in which at least two through holes 3 are formed in the tube 2. In other words, the present invention can be applied to all types of cuff-equipped tubes by which a surgical procedure is carried out to a patient while using a cuff capable of performing an expansion and a contraction.

That is, the present invention can be applied to all of the cuff-equipped tubes that are used for not only a medical procedure of a trachea and a bronchial tube but also a medical procedure of a blood vessel, a bile duct, an esophagus, a respiratory tract, a urethra, a living organism lumen of other organ, and a body cavity.

What is claimed is:

1. A cuff-equipped tube comprising a cuff affixed to an outer peripheral surface of a flexible tube, the cuff being expanded radially by introducing an operation fluid thereinto or being contracted radially by discharging the operation fluid therefrom, wherein the cuff is provided with a cuff affixing portion that is expanded radially outward by the introduction of the operation fluid thereinto, and also with a first mounting portion and a second mounting portion mounted to the outer peripheral surface of the tube, the first mounting portion and the second mounting portion having an outer diameter smaller than an outer diameter of the cuff affixing portion, the first mounting portion is connected by a first side wall with the cuff affixing portion to define a first overlapping region, and the first mounting portion is directly affixed to the outer peripheral surface of the tube, and the second mounting portion is connected by a second side wall with the cuff affixing portion to define a second overlapping region, and the second mounting portion is directly affixed to the outer peripheral surface of the tube, and in the case in which an external force is applied to the tube in an axial direction in a state in which the operation fluid is introduced to the cuff affixing portion and the cuff affixing portion is expanded such that the tube is displaced by a distance equal to or less than a length of the first overlapping region and the second overlapping region, the distance between the first mounting portion and the second mounting portion is constant and does not change, the first side wall and the second side wall are deformed from a first axial position to a second axial position by a distance corresponding to a displacement of the tube while the cuff affixing portion is maintained at a predetermined position, and in the case in which the external force that has been applied to the cuff is removed, the first side wall and the second side wall return to an original posture, wherein the cuff is formed in a generally barrel shape in which the cuff affixing portion is expanded to the both sides from an axis core as a center, and the first mounting portion and the second mounting portion are extended outward in an axis direction of the cuff affixing portion in a generally barrel shape, and in the case in which the cuff is affixed to the outer peripheral surface of the tube, the first side wall connecting the first mounting portion with the cuff affixing portion is connected with the first mounting portion in such a manner that the first side wall is urged toward a side of the cuff affixing portion so as to form a cross-sectional Z shape, the second side wall connecting the second mounting portion with the cuff affixing portion is connected with the second mounting portion in such a manner that the second side wall is urged toward a side of the cuff affixing portion so as to form a cross-sectional Z shape, and a width of the cross-sectional Z shape is 3 mm or more, and a length of the cross-sectional Z shape is determined according to a movable length of the cuff.

2. A cuff-equipped tube as defined in claim 1, wherein the cuff affixing portion, the first mounting portion, and the second mounting portion are formed in a generally cylindrical shape.

* * * * *